United States Patent [19]

Rucman

[11] 4,230,859
[45] Oct. 28, 1980

[54] PROCESS FOR THE PREPARATION OF N-SUBSTITUTED ESTERS OF 9,10-DIHYDROLYSERGICACIDS

[75] Inventor: Rudolf Rucman, Ljubljana, Yugoslavia

[73] Assignee: LEK, tovarna farmacevtskih in kemicnih izdelkov, n.sol.o., Ljubljana, Yugoslavia

[21] Appl. No.: 922,692

[22] Filed: Jul. 7, 1978

[30] Foreign Application Priority Data

Jul. 21, 1977 [YU] Yugoslavia .......................... 1819/77

[51] Int. Cl.$^2$ .......................................... C07D 457/04
[52] U.S. Cl. ........................................................ 546/69
[58] Field of Search ......................................... 546/69

[56] References Cited

U.S. PATENT DOCUMENTS

| | | | |
|---|---|---|---|
| 3,218,324 | 11/1965 | Hofmann et al. ................ | 546/69 |
| 3,228,943 | 1/1966 | Bernardi et al. ................. | 546/67 |
| 3,232,942 | 2/1966 | Hofmann et al. ................ | 260/285.5 |
| 3,755,328 | 8/1973 | Stadder et al. ................... | 546/69 |
| 3,879,554 | 4/1975 | Temperilli ........................ | 424/261 |
| 3,966,739 | 6/1976 | Bernardi et al. ................. | 546/67 |

FOREIGN PATENT DOCUMENTS

631701  11/1961  Canada ................. 260/285.5

OTHER PUBLICATIONS

Troxler et al; Helv. Chim. Acta; vol. 40, p. 2160–2170 (1957).

*Primary Examiner*—Mary C. Lee
*Attorney, Agent, or Firm*—Pollock, Vande Sande & Priddy

[57] ABSTRACT

A process for the preparation of N-substituted esters of 9,10-dihydrolysergic acids of the formula:

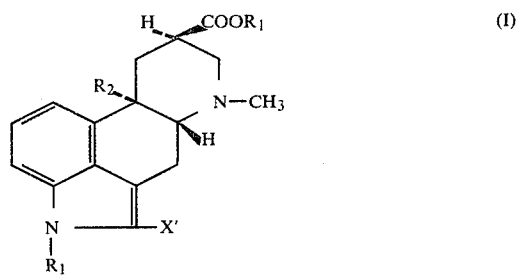

wherein
$R_1$ is an alkyl group of 1–5 carbon atoms, an alkenyl group of 2–5 carbon atoms or a cycloalkyl group of 3–5 carbon atoms,
$R_2$ is hydrogen or an alkoxy group of 1–3 carbon atoms and
$X'$ is hydrogen or halogen, characterized in that esterified 9,10-dihydrolysergic acids of the formula:

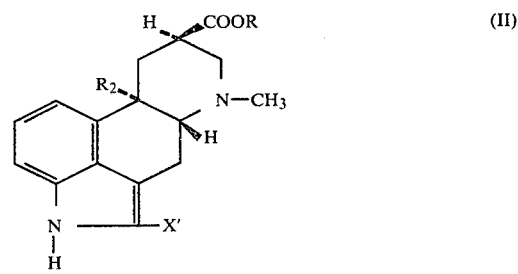

wherein
R is hydrogen or a hydrolyzable organic group,
$X'$ is hydrogen or halogen, and
$R_2$ has the meaning as stated above, are reacted with a compound of the formula:

$R_1Y$         (III)

wherein
$R_1$ has the meaning as stated above,
Y is halogen or sulphate, in the presence of a catalyst for phase transition in the presence of aqueous alkali medium in an inert organic solvent immiscible with water, and certain novel esters obtained thereby.

24 Claims, No Drawings

PROCESS FOR THE PREPARATION OF N-SUBSTITUTED ESTERS OF 9,10-DIHYDROLYSERGIC ACIDS

The present invention relates to an improved process for the preparation of intermediates for the synthesis of certain pharmacologically active compounds. In particular, it relates to an improved process in an N-alkylation step for the preparation of intermediates of the formula I.

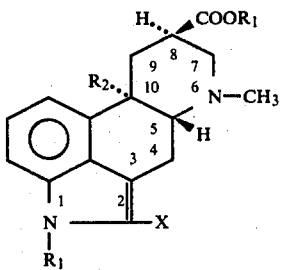

wherein
$R_1$ is an alkyl radical containing 1–5 carbon atoms, an alkenyl radical containing 2–5 carbon atoms or a cycloalkyl radical containing 3–5 carbon atoms,
$R_2$ is hydrogen or an alkoxy radical containing 1–3 carbon atoms, and
X is hydrogen or halogen.

The hitherto known process for N-alkylation of lysergic acids or other compounds with this basic structure is based on metallisation of indol nitrogen with metallic potassium or lithium in liquid ammonia at $-50°$ C., followed by the introduction of an alkyl radical. According to this process, the alkyl radical is introduced only in 1-position. As the reaction is not very selective, at the necessary excess of alkylhalide it is also accompanied by the substitution of the activated hydrogen at the chirality centre 8 with an alkyl radical so that the yield of the N-alkyl compound is lower (F. Troxler and A. Hofmann, Helv. chim. Acta 40, 1957, 1721). The work at the cited reaction conditions is pretentios, anhydrous solvents are needed and at unfavourable conditions there can also occur explosions. The reaction product must be purified by column chromatography.

The inventive process for preparing N-alkylated esters of 9,10-dihydrolysergic acids according to the formula I comprises the alkylation of the compounds of the formula II.

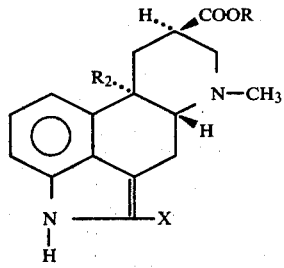

wherein
R is hydrogen or an organic radical which is hydrolysable in alkaline medium and
X and $R_2$ have the meaning as cited under formula I, with a compound of the general formula $$R_1Y \qquad (III)$$

wherein
$R_1$ has the meaning as cited under formula I and
Y is halogen or sulphate,
in the presence of a catalyst for phase transition, of an inert organic solvent which is immiscible with water and of alkali aqueous phase.

According to the inventive process, there is simultaneously introduced the alkyl alkenyl or cycloalkyl group in 1-position of the compound of the general formula II and the radical in 8-position when a carboxylic group is esterified with the same alkyl alkenyl or cycloalkyl group as introduced in 1-position.

In the compound of the general formula II R is hydrogen or an organic radical which is hydrolysable in alkaline medium. For the process according to the invention there can also be used esters of 9,10-dihydrolysergic acids wherein R is any organic radical which is higher than the introduced radical $R_1$. By the intermediate alkaline hydrolysis, this organic radical R can be substituted by a lower radical $R_1$.

The compounds of the general formula II and III are known and described in the literature or they can be obtained by processes which are known in the art.

The starting substances of the formula II are alkylated with compounds of the formula III in the presence of a catalyst for phase transition. This catalyst is an ammonium or phosphonium compound of the general formula $Z_4QA$, wherein Z represents equal or different alkyl, cycloalkyl, aryl, arylalkyl or alkylaryl radicals containing 1–16 carbon atoms, Q is a quaternary nitrogen or phosphorus atom and A is an anion, such as chloride, bromide, iodide, hydrogen sulphate, acetate, tosylate etc. As the catalysts for phase transition there can be used e.g.
tetrabutylammonium bromide,
tetrabutylammonium hydrogen sulphate
triethylbenzylammonium chloride
tricaprylylmethylammonium chloride,
tetrabutylphosphonium bromide, etc.

The catalyst for phase transition is used in a quantity of 0.1 to 3 moles for 1 mole of 9,10-dihydrolysergic acid. The quantity of the catalyst in this range highly influences the reaction rate. As 9,10-dihydrolysergic acids and derivatives thereof are very sensitive compounds, a fast course of the reaction is desirable. Therefore a quantity of the catalyst which is near to the cited upper limit should be preferably used.

As the water-immiscible inert organic solvent, benzene, toluene, xylene or a saturated hydrocarbon, such as pentane, hexane, heptane or cyclohexane, can be used.

The alkaline water phase is a 20 to 50% water solution of an alkali hydroxide, e.g. sodium hydroxide.

The process according to the invention can be executed at ambient or moderately elevated temperature.

The substitution of the carboxylic hydrogen 9,10-dihydrolysergic acids in 8-position is faster than the substitution in 1-position. At the beginning of the reaction, the ester and the N-substituted ester can be isolated from the reaction mixture. At the continuation of the reaction, the concentration of the ester is lowered until, at the end of the reaction, it completely disappears and only N-substituted ester is obtained. At the introduction of alkyl or alkenyl and cycloalkyl radical into the alkyl- or alkenyl-and cycloalkylester of 9,10-dihydrolysergic acid there is therefore obtained alkyl-, alkenyl- or cycloalkylester of 1-(alkyl- or alkenyl- or cycloalkyl)-9,10-dihydrolysergic acid in a high yield.

The advantages of the process according to the invention in comparison with the known process are good selectivity, simple and fast reaction course which can be easily controlled, the use of usual solvents from which water need not be removed and, above all, the reaction conditions which allow safe work at room temperature in aqueous medium.

The compounds according to the invention are important intermediates for synthesis of therapeutically highly effective compounds with N-substituted radical in 1-position. Further synthesis reactions are in the first place the reduction of ester radical in 8-position into primary alcoholic radical, which is then combined with a radical of an appropriate acid, e.g. of 5-bromonicotinic acid. Hence it is very favourable to have the simultaneous introduction of the radical $R_1$ into 1-position and esterification of carboxylic radical in 8-position, which thereby becomes more accessible for the reduction into alcoholic radical.

EXAMPLE 1

2.7 g. (10 mmoles) of 9,10-dihydrolysergic acid and 7 g. (20 mmoles) of tetrabutylammonium hydrogen sulphate are suspended in 200 ml. of 45% sodium hydroxide. The solution of 4.2 g. (30 mmoles) of methyl iodide in 300 ml. of benzene is added and it is vigorously stirred for 1 hour. Then the organic phase is separated and the water phase is extracted in the same way with 2×150 ml. of benzene containing 2.1 g. (15 mmoles) of methyl iodide. Benzene extracts are combined, washed with water until the reaction is neutral, and the solvent is evaporated. There are obtained 2.62 g. or 88% of the theory of pure, crystalline methyl 1-methyl-9,10-dihydrolysergate with a m.p. of 116° to 119° C. and a specifical rotation of $/\alpha/_D{}^{20} = -61.1°$ (c=0.5, chloroform).

EXAMPLE 2

To a two phase system containing 200 ml. of 50% sodium hydroxide, 7 g. (2 mmoles) of tetrabutylammonium hydrogen sulphate, 2.8 g (20 mmoles) of methyl iodide and 300 ml. of benzene, under vigorous stirring there are added 2.84 g. (10 mmoles) of methyl 9,10-dihydrolysergate. It is stirred for 30 minutes and then the phases are separated. 200 ml. of benzene containing 2.1 g. (15 mmoles) of methyl iodide are added to the water phase and stirring is continued for further 30 minutes. Then the two phases are separated and the water phase is extracted with 2×150 ml. of benzene. The four benzene extracts are washed with water until the reaction is neutral, and evaporated. There are obtained 2.7 g. or 91% of the theory of pure, crystalline methyl 1-methyl-9,10-dihydrolysergate. The compound has the same properties as in Example 1.

EXAMPLE 3

2.7 g. (10 mmoles) of 9,10-dihydrolysergic acid and 6.44 g. (20 mmoles) of tetrabutylammonium bromide are suspended in 20 ml. of 45% sodium hydroxide. A solution of 3.78 g. (30 mmoles) of dimethyl sulphate in 300 ml. of benzene is added and stirred vigorously for 1 hour. Then the organic phase is separated and the water phase is extracted in the same way with 2×150 ml. of benzene containing 2.1 g. (15 mmoles) of methyl iodide. Benzene extracts are combined, washed with water until the reaction is neutral, and evaporated in vacuo. 2.36 g. or 82.6% of the theory of pure, crystalline methyl 1-methyl-9,10-dihydrolysergate are obtained. The compound has the same properties as in Example 1.

EXAMPLE 4

2.7 g. (10 mmoles) of 9,10-dihydrolysergic acid and 7 g. (20 mmoles) of tetrabutylammonium hydrogen sulphate are suspended in 200 ml. of 45% sodium hydroxide and a solution of 4.62 g. (30 mmoles) of diethyl sulphate in 300 ml. of toluene is added. It is vigorously stirred for 8 hours at ambient temperature. Then the organic phase is separated and, in the same way, the water phase is extracted for 4 hours with 300 ml. of toluene containing 1.54 g. (10 mmoles) of diethyl sulphate. The toluene extracts are combined, washed with water until the reaction is neutral, an evaporated in vacuo. 2.15 g. or 68.7% of the theory of pure, crystalline ethyl 1-ethyl-9,10-dihydrolysergate are obtained with a m.p. of 80° to 82° C. and a specifical rotation of $/\alpha/_D{}^{20} = -70.6°$ (c=0.5, chloroform).

EXAMPLE 5

2.7 g. (10 mmoles) of 9,10-dihydrolysergic acid and 7 g. (20 mmoles) of tetrabutylammonium hydrogen sulphate are suspended in 200 ml. of 45% sodium hydroxide, a solution of 4.85 g. (40 mmoles) of allyl bromide in 300 ml. of benzene is added and it is stirred vigorously for 2 hours. Then the phases are separated and the water phase is extracted in the same way with 2×200 ml. of benzene containing 2.42 g. (20 mmoles) of allyl bromide. The benzene extracts are combined, washed with water until the reaction is neutral, and evaporated in vacuo. 2.3 g. or 66% of theory of allyl 1-allyl-9,10-dihydrolysergate are obtained in the form of a colourless resin with a specifical rotation of $/\alpha/_D{}^{20} = -69.9°$ (c=0.5, chloroform).

EXAMPLE 6

0.3 g. (1 mmole) of 10alpha-methoxy-lumilysergic acid and 0.7 g. (2 mmoles) of tetrabutylammonium hydrogen sulphate are suspended in 20 ml. of 45% sodim hydroxide and this suspension is extracted with 3×30 ml. of benzene containing 0.42 g. (3 mmoles) of methyl iodide, each time under vigorous stirring for 1 hour. The combined benzene extracts are washed with water and evaporated in vacuo. 0.25 g. or 77% of the theory of methyl 1-methyl-10alpha-methoxy-lumilysergate are obtained in the form of a colourless resin with a specifical rotation of $/\alpha/_D{}^{20} = +9°$ (c=0.5, chloroform).

EXAMPLE 7

A mixture of 4.5 g. (13.22 mmoles) of methyl 10alpha-methoxylumilysergate, 8.67 g. (26.44 mmoles) of tetrabutylammonium hydrogen sulphate, 200 ml. of 45% sodium hydroxide, 300 ml. of toluene and 3.33 g. (26.44 mmoles) of dimethyl sulphate is vigorously stirred for 20 minutes at 30° C. Then the toluene phase is separated from the water phase and extracted with 3×200 ml. of toluene containing 1.66 g. (13.22 mmoles) of dimethyl sulphate, each time under vigorous stirring for 20 minutes at 30° C. The combined toluene extracts are washed with water and evaporated in vacuo. 3.8 g. of methyl 1-methyl-10alpha-methoxy-lumilysergate are obtained in the form of a colourless resin with a specifical rotation of $/\alpha/_D{}^{20} = +8.7°$ (c=0.5, chloroform).

EXAMPLE 8

To a suspension of 140 ml. of 45% sodium hydroxide, 4.87 g. (14.3 mmoles) of tetrabutylammonium hydrogen sulphate, 215 ml. of benzene and 3 g. (21.5 mmoles) of methyl iodide, there are added 2.6 g. (7.16 mmoles) of methyl 2-bromo-9,10-dihydrolysergate in 65 ml. of benzene under vigorous stirring at 35° C. The solution is stirred for 30 minutes, then the organic phase is separated from the water phase. The water phase is extracted with 2×150 ml. of benzene containing 1.5 g. (10.7 mmoles) of methyl iodide. The combined benzene extracts are washed with water and evaporated in vacuo. The dry residue is crystallized form methanol. 2.42 g. or 90% of the theory of crystalline methyl 1-methyl-2-bromo-9,10-dihydrolysergate are obtained with a m.p. of 167°–168° C. and a specifical rotation of $/\alpha/_D^{20} = -94.2°$ (c=0.5, chloroform).

EXAMPLE 9

To a suspension of 80 ml. of 45% sodium hydroxide, 3.5 g. (10 mmoles) of tetrabutylammonium hydrogen sulphate, 200 ml. of cyclohexane and 3.51 g. (22.5 mmoles) of ethyl iodide, there are added 1.45 g. (5 mmoles) of ethyl 9,10-dihydrolysergate under stirring. It is vigorously stirred for 18 hours at 60° C. After the separation of the two phases, the water phase is extracted with 150 ml. of cyclohexane containing 1.56 g. (10 mmoles) of ethyl iodide. The cyclohexane fractions are combined, washed with water and evaporated. 1.22 g. or 80% of the theory of ethyl 1-ethyl-9,10-dihydrolysergate are obtained with a m.p. of 80°–83° C. and a specifical rotation of $/\alpha/_D^{20} = -70°$ (c=0.5, chloroform).

EXAMPLE 10

In a two-phase system comprising 200 ml. of 45% sodium hydroxide, 7 g. (20 mmoles) of tetrabutylammonium hydrogen sulphate, 200 ml. of toluene and 2.52 g. (20 mmoles) of dimethyl sulphate, there is added under vigorous stirring a solution of 3.16 g. (10 mmoles) of 2'-fluoroethyl 9,10-dihydrolysergate in 100 ml. of toluene and it is stirred for 2 hours. The toluene extract is separated from the water solution which is then extracted with 2×200 ml. of toluene containing 0.63 g. (5 mmoles) of dimethyl sulphate. The combined toluene extracts are washed with water and evaporated to dryness in vacuo. 2.14 g. or 71.8% of the theory of crystalline methyl 1-methyl-9,10-dihydrolysergate are obtained. The compound has the same properties as cited in Example 1.

What is claimed is:

1. In a process for the preparation of N-substituted esters of 9,10-dihydrolysergic acids of the formula:

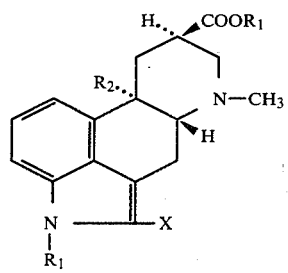

capable of being converted to pharmacologically active compounds wherein $R_1$ is an alkyl group of 1–5 carbon atoms, an alkenyl group of 2–5 carbon atoms, or a cycloalkyl group of 3–5 carbon atoms, $R_2$ is hydrogen or an alkoxy group of 1–3 carbon atoms, and X is hydrogen or halogen, the improvement which comprises carrying out the alkylation of the compounds of the formula:

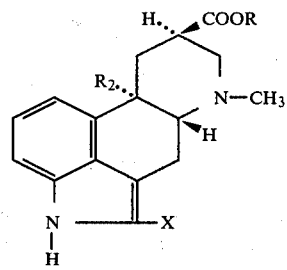

wherein

R is hydrogen or a hydrolyzable organic group capable of being hydrolyzed in alkaline medium, X is hydrogen or halogen, and $R_2$ has the meaning as stated above, with a compound of the formula:

$R_1Y$         (III)

wherein $R_1$ has the meaning as stated above,

Y is halogen or sulphate, in the presence of a catalyst for phase transition of the formula:

$Z_4QA$         (IV)

wherein

Z represents the same or different alkyl, cycloalkyl, aryl, arylalkyl or alkylaryl groups with 1–16 carbon atoms, Q is an quaternary nitrogen or phosphorus atoms, and A is an anion, in a two phase aqueous alkali medium-organic solvent system wherein the organic phase includes a hydrocarbon which is immiscible with water.

2. The process of claim 1 wherein the amount of catalyst is 0.1 to 3 moles per mole of said compounds of formula II.

3. The process of claim 1 wherein said aqueous alkali medium is a 20 to 50% water solution of an alkali hydroxide.

4. The process of claim 3 wherein said alkali hydroxide is sodium hydroxide.

5. The process of claim 1 wherein said inert organic solvent includes benzene, toluene, xylene, or a saturated hydrocarbon.

6. The process of claim 5 wherein said saturated hydrocarbon includes pentane, hexane, heptane, or cyclohexane.

7. The process of claim 1 wherein said catalyst includes tetrabutyl ammonium bromide or tetrabutyl ammonium hydrogen sulphate, or triethyl benzyl ammonium chloride, or tricaprylyl methyl ammonium chloride, or tetrabutyl phosphonium bromide.

8. The process of claim 1 wherein said compound of the formula (III) includes methyl iodide.

9. The process of claim 1 wherein said compound of the formula (III) includes ethyl iodide.

10. The process of claim 1 wherein said compound of the formula (III) includes allyl bromide.

11. The process of claim 1 wherein said compound of the formula (III) includes dimethyl sulphate.

12. The process of claim 1 wherein said compound of the formula (III) includes diethyl sulphate.

13. The process of claim 1 wherein said compounds of the formula (II) include 9,10-dihydrolysergic acid.

14. The process of claim 1 wherein said compounds of the formula (II) include methyl-9,10-dihydrolysergate.

15. The process of claim 1 wherein said compounds of the formula (II) include 10α-methoxy-lumilysergic acid.

16. The process of claim 1 wherein said compounds of the formula (II) include methyl-10α-methoxy-lumilysergate.

17. The process of claim 1 wherein said compounds of the formula (II) include methyl-2-bromo-9,10-dihydrolysergate.

18. The process of claim 1 wherein said compounds of the formula (II) include ethyl-9,10-dihydrolysergate.

19. The process of claim 1 wherein said esters of the formula (I) include methyl-1-methyl-9,10-dihydrolysergate.

20. The process of claim 1 wherein said esters of the formula (I) include ethyl-1-ethyl-9,10-dihydrolysergate.

21. The process of claim 1 wherein said esters of the formula (I) include allyl-1-allyl-9,10-dihydrolysergate.

22. The process of claim 1 wherein said esters of the formula (I) include methyl-1-methyl-10α-methoxy-lumilysergate.

23. The process of claim 1 wherein said esters of the formula (I) include methyl-1-methyl-2-bromo-9,10-dihydrolysergate.

24. The process of claim 1 wherein said anion includes chloride, or bromide, or iodide, or hydrogen sulphate, or acetate, or tosylate.

* * * * *